(12) United States Patent
Humbert et al.

(10) Patent No.: US 8,683,861 B2
(45) Date of Patent: Apr. 1, 2014

(54) HUMIDITY SENSOR BASED ON PROGRESSIVE CORROSION OF EXPOSED MATERIAL

(75) Inventors: Aurelie Humbert, Brussels (BE); Youri Victorovitch Ponomarev, Leuven (BE); Matthias Merz, Leuven (BE); Romano Hoofman, Geel (BE)

(73) Assignee: NXP, B.V., Eindhoven (NL)

( * ) Notice: Subject to any disclaimer, the term of this patent is extended or adjusted under 35 U.S.C. 154(b) by 377 days.

(21) Appl. No.: 12/670,715

(22) PCT Filed: Jul. 30, 2008

(86) PCT No.: PCT/IB2008/053059
§ 371 (c)(1),
(2), (4) Date: Jan. 26, 2010

(87) PCT Pub. No.: WO2009/016594
PCT Pub. Date: Feb. 5, 2009

(65) Prior Publication Data
US 2010/0192688 A1      Aug. 5, 2010

(30) Foreign Application Priority Data
Aug. 2, 2007 (EP) ..................... 07113671

(51) Int. Cl.
G01N 19/00 (2006.01)
(52) U.S. Cl.
USPC .......................... 73/335.03; 422/53
(58) Field of Classification Search
USPC .......................... 73/335.03; 422/53
See application file for complete search history.

(56) References Cited

U.S. PATENT DOCUMENTS

| | | | |
|---|---|---|---|
| 3,056,935 A * | 10/1962 | Jensen | 338/35 |
| 4,562,725 A * | 1/1986 | Oka et al. | 73/29.05 |
| 4,891,574 A * | 1/1990 | Nagaya et al. | 324/664 |
| 4,965,698 A | 10/1990 | Thoma et al. | |
| 5,028,906 A * | 7/1991 | Moriya et al. | 338/35 |
| 5,338,432 A * | 8/1994 | Agarwala et al. | 205/118 |
| 5,446,369 A * | 8/1995 | Byrne et al. | 324/71.2 |
| 6,383,451 B1 | 5/2002 | Kim et al. | |
| 6,564,620 B1 | 5/2003 | Jaeger | |
| 7,388,386 B2 * | 6/2008 | Ramgopal et al. | 324/700 |
| 2003/0029232 A1 | 2/2003 | Felix et al. | |
| 2006/0006137 A1 | 1/2006 | Niblock | |
| 2006/0125493 A1 | 6/2006 | Subramanian | |
| 2006/0162431 A1 | 7/2006 | Harris et al. | |
| 2006/0213264 A1 | 9/2006 | Ku et al. | |

FOREIGN PATENT DOCUMENTS

CN    1455250 A    11/2003
JP    2002062252 A    2/2002

OTHER PUBLICATIONS

Lin, Xue-Yan, et al; "Dust Corrosion"; Electrical Contacts; 2004 Proceedings of the 50th IEEE Holm Conference on Electrical Contacts and the 22nd Int'l Conference on Electrical Contacts; Sep. 20-23, 2004; pp. 255-262.

* cited by examiner

Primary Examiner — Herzon E Williams
Assistant Examiner — Rodney T Frank

(57) ABSTRACT

A sensor senses a characteristic of an environment, e.g., humidity. The sensor has a substrate with strips of material that is sensitive to corrosion as a result of the characteristic. The strips are configured to respond differently to the characteristic. By means of repeatedly measuring the resistances of the strips, the environment can be monitored in terms of accumulated exposure to the characteristic. The strips are manufactured in a semiconductor technology so as to generate accurate sensors that behave predictably.

17 Claims, 5 Drawing Sheets

HUMIDITY SENSOR BASED ON PROGRESSIVE CORROSION OF EXPOSED MATERIAL

FIELD OF THE INVENTION

The invention relates to an electronic circuit comprising a sensor to sense a characteristic, e.g., humidity or contamination (e.g., dust or a specific chemical compound such as ammonia), of the environment of the sensor, and to a method of sensing this characteristic.

BACKGROUND ART

Humidity sensing is of great importance in many industrial applications, including monitoring of pharmaceutical, biomedical, food/beverage storage and logistics, electronics, automotive and semiconductors industries. For the food monitoring application for example, measuring the relative humidity inside the package is necessary to monitor the quality of the product, as excessive moisture content may lead to premature spoilage. In such application, the miniaturization of the sensors is also a key element.

The vast majority of the humidity sensors nowadays commercially available are capacitive sensors. Such sensors use a material, whose dielectric constant change as a function of relative humidity, and the corresponding change of the capacitance is recorded. However, the dependence of the capacitance on relative humidity is in most cases not linear and substantial hysteresis is usually encountered at high humidity values, due to a slower diffusion time in the moisture sensitive film during the dehumidifying process.

An alternative to a capacitive sensor is a resistive sensor. The basic configuration is the same as that of a capacitive humidity sensor, but the dielectrics layers are replaced by conducting layers whose conductivity depends on the absolute or relative humidity values. In this case, humidity measurements hysteresis still remains a problem, especially if the sensors are not used continually. Long-term stability of the sensor can only be guaranteed by continual operation and attentive maintenance. In, e.g., industrial applications, shelf life before usage of the sensor is an unknown factor.

Humidity sensors are known from, e.g., following patent publications, all incorporated herein by reference.

CN1455250 discloses a sensor that comprises a substrate, an oxide layer and a capacitance electrode. The oxide layer is on the substrate and the capacitance electrode with the lead wire is on the oxide layer. The capacitance electrode is made from the material suitable to the technique of preparing standard CMOS. The passivation layer is setup on the capacitance electrode. The comb type parallel structure of the aluminum anode increases the sensing value of the capacitance. The substrate connected to the ground reliably eliminates interference outside so as to raise the accuracy. The deposited passivation layer prevents the electrode from corrosion of water vapor absorbed by polyimide. The heating circuit prepared by using the comb type parallel polysilicon makes desorption time shorter. This configuration provides the advantages of high sensitivity, linearity, good hysteresis and reliability for a long time.

JP2002062252 addresses as the problem to be solved: to quickly and inexpensively diagnose in real-time a life and a degree of deterioration of equipment having a metallic portion to provide a recipe for maintenance of the equipment. This document proposes a system that has an environment sensor group for measuring environmental factors in the environment where the equipment having the metallic portion is installed, a diagnostic client for monitoring outputs of sensors, a diagnostic server for estimating the life and the degree of the deterioration based on the sensor outputs transmitted from the diagnostic client via the Internet to provide a diagnostic result therein and the recipe to the diagnostic client via the Internet, and a diagnostic database accumulated with a data group required for diagnosis.

US published patent application 20060213264 teaches the following.

Conventionally, for preventing electric devices from dewing and from short circuits resulting from water cooling systems therein, the electric devices include dewing sensors to detect the vapor saturation that cause a feedback control signal to be sent for driving excitators. The characteristic curves of the conventional dewing sensors, however, are too smooth to detect the dewing reaction when the humidity is between 89-90% relative humidity. Furthermore, because of the high cost of the conventional dewing sensors made of metallic oxides by integrated circuit process, the conventional dewing sensors are not extensively used in some low-cost electrical devices. Another dewing sensor is proposed. The dewing sensor includes a substrate having at least two electrodes, at least two comb electrodes, and a detecting layer. The comb electrodes contact the two electrodes on the substrate, and the detecting layer includes a derivative of cellulose formed on the comb electrodes. For detecting the humidity, the two electrodes of the dewing sensor are fastened by a clamping apparatus and connected to a multimeter. The temperature and humidity are determined by a standard temperate-humidity controller. After stabilizing the dewing sensor, the impedance between the electrodes of the dewing sensor is output.

U.S. Pat. No. 4,965,698 discloses a capacitance humidity sensor with a dielectric film core which is in contact with a pair of polymeric conductive layers bonded to opposite faces of the core. The dielectric core is made of a polymeric material having a dielectric constant which varies substantially linearly with humidity, such as a polyimide or polyparabanic acid. The conductive layers are made of a polymeric material having conductive particles, such as carbon particles, dispersed therein. Such conductive layers provide superior performance and corrosion resistance in comparison to the metal films commonly employed at that time.

SUMMARY OF THE INVENTION

The inventors provide an alternative to the known sensors, among which above humidity sensors. Their insight is based on the publication "Dust corrosion", by Xue-Yan Lin and Ji-Gao Zhang, Electrical Contacts, 2004, Proceedings of the $50^{th}$ IEEE Holm Conference on Electrical Contacts and the $22^{nd}$ International Conference on Electrical Contacts, published 20-23 September, 2004, pages 255-262. This publication relates to an investigation of general corrosion, also referred to as uniform corrosion. General corrosion is one of the most common types of corrosion. It damages the entire surface of the material at about the same rate, causing the material to thin. Controlling general corrosion is relatively easy. However, if not controlled, the metal surface continues to thin until nothing is left. The publication teaches a characteristic dependence of corrosion of the features in an integrated circuit on relative humidity and chemical contamination of the circuit's environment. The publication's conclusion is that humidity better be controlled in order to guarantee flawless operation of the integrated circuit.

The inventors now turn the corrosion concept upside down and propose to use the characteristic dependence as a reference to measure or monitor a characteristic of the circuit's environment, e.g., relative humidity and/or presence of chemicals in airborne dust, etc. More particularly, the inventors propose a device comprising a sensor for sensing a characteristic of an environment of the sensor. The sensor has a substrate with a strip of material that is sensitive to corrosion as a result of the characteristic. The strip is arranged between two contacts for measuring an impedance of the strip.

By measuring the resistance of the strip twice or more over time, the rate of corrosion can be estimated based on the increasing resistance as measured. These accumulated measurements then represent a history log of the exposure of the sensor's material to the environment.

An embodiment of the sensor uses the corrosion characteristics of a material to track the humidity content of the atmosphere. Indeed, corrosion is dependent on moisture content. An example of such dependence is given in FIG. 13 of the publication by Lin and Zhang. Their FIG. 13 shows a roughly linear dependence of the corrosion ratio on the relative humidity in the relative humidity range between roughly 10% and 90%. The corrosion ratio is defined as the number of dust particles causing corrosion divided by the total number of dust particles per unit of area. As a consequence of corrosion, the material will gradually thin, making it possible to evaluate the humidity content or humidity history by measuring at intervals the resistance increase of the electrodes made of such corroding material. The most significant advantage of such sensor element is complete absence of hysteresis as the conducting material is simply consumed during operation with the rate directly proportional to the absolute humidity in the ambient atmosphere of the sensor.

The materials susceptible to corrosion and suitable for use in a sensor of the invention include, e.g., nickel (Ni), copper (Cu), zinc (Zn), lead (Pb), iron (Fe), cobalt (Co), or silver (Ar), etc., or other materials typically used in implementing an electrical contact at an integrated circuit can be used as well in the sensor of the invention (e.g., aluminum (Al)).

A further embodiment of the invention relates to a device as specified above, wherein the sensor comprises at least one further strip of a further material sensitive to corrosion and arranged between two further contacts for measuring the impedance of the further strip, and wherein the strip and the further strip are configured to have impedances that respond differently to the characteristic.

In this embodiment, multiple strips are being used whose resistances respond differently to the characteristic. For example, the strips have differently sized surfaces exposed to the environment, but the same path lengths between their respective contacts. Corrosion will sooner affect the Ohmic resistance noticeably of the strip that has the narrower path between its contacts. The strip with the narrowest path will typically fail before another strip with a wider path, assuming that the strips are chemically of the same material. As another example, the materials of the strips are chemically different. Then, the Ohmic resistance of the strip with the higher sensitivity to corrosion will be affected sooner than the resistance of a strip made of a material with a lower sensitivity. As another example, the strips have different thicknesses. Thickness of a strip is defined within this context as, e.g., the strip's dimension in a direction perpendicular to its surface exposed to the environment. The thinner one of the strips will fail before a thicker one, assuming that the strips are chemically of the same material and geometrically uniform. This, however, may require too many process steps in a semiconductors manufacturing process in order for such an implementation to be economically attractive.

Accordingly, in a sensor with multiple strips, geometrical dimensions and/or material can be chosen per individual strip so as to suit the intended purpose of the sensor. Another feature that can be varied is the path length of the strip. In an example embodiment, a strip is shaped so as to have the shortest path between its contacts. For example, multiple strips are arranged in parallel between pairs of equidistant contacts. In another embodiment, the strip has a meandering path between its contacts, so as to have a presence over a larger area. In that case, the location of the strip with respect to the substrate becomes less relevant to the strip's functionality of a corrosion-driven sensor. Multiple strips can be made with uniformly shaped paths.

Preferably, the strips are manufactured in a semiconductors technology process including, e.g., electroplating, chemical vapor deposition, lithographic steps, etching, etc. In this manner a well matured and optimized manufacturing technology is used to create highly predictable products that can be calibrated accurately.

An example embodiment uses an array of electrodes with different sizes. Depending on the moment in time when the sensing capability is needed, the corrosion process has probably already started. However, with different sizes in the structure, one can still find the best electrode to have optimal sensitivity (the thinnest not fully corroded line). It would be advantageous to monitor the resistance of at least two electrodes to ensure continuity and possibility of error corrections to improve sensitivity. The calibration of the sensor will be needed at the point of monitoring start, if not only variation of humidity levels are monitored but the actual humidity levels are needed to be measured.

A sensor in the invention can be implemented as a passive device, i.e., in order to determine the degree of corrosion, the device is to be subjected to a measurement using an external apparatus. Alternatively, the sensor of the invention comprises circuitry that is kept electrically active during the time period over which one wants to monitor the progress of corrosion. When an electrode breaks down due to corrosion, the sensor generates a warning signal to be detected by an outside agent, e.g., a human operator. In yet another embodiment, the sensor of the invention is used in an RFID (radio-frequency identification) device. RFID technology is a widely known method for remotely retrieving data via a transponder. The RFID device of the invention is then configured to transfer the information about corrosion progress when read out by a remote reader, and/or to generate a warning if a pre-determined threshold has been crossed.

Instead of the Ohmic resistance, another type of impedance (e.g., inductance or capacitance) can be measured, so long this impedance is affected by the corrosion of the material exposed to the environment. For example, an inductance can be excited by means of an electromagnetic field generated by a remote agent. Such an approach is being used with labels attached to merchandize in a store. A gate at the store's exit produces an electromagnetic field that causes an inductor in circuitry embedded in the label to generate another harmonic of the incident field. This higher harmonic field is sensed by the gate which thereupon triggers an alarm. Now, within the context of the present invention, this scenario is applied with some changes. That is, a transmitter generates an electromagnetic field to excite one or more inductors made of strips in a sensor as set forth above. A receiver receives the inductors response to being excited with this field. If one or more of the strips have been corroded enough as a result of the exposure to the environment, the sensor's response will have changed accordingly. Again, this response (or its absence) is then indicative of the accumulated exposure to the sensor's environment. Therefore, where the expression "Ohmic resistance" has been used throughout this text, the skilled person understands that inductance or capacitance is an alternative quantity, whose measured value is indicative of the corrosion accumulating as a result of a prolonged exposure to the environment.

The invention further relates to a method of sensing a characteristic of an environment, the method comprising: using a material that is sensitive to corrosion as a result of the characteristic; measuring an impedance of the material as a quantity indicative of an exposure of the material to the environment. In an embodiment of such a method, a further material is used sensitive to corrosion. The material and the further material are configured to have impedances that respond differently to the characteristic. The method comprises measuring the impedances of the material and the further material on at least two different moments. The measurements are then to be compared with calibration or reference information, prepared in advance, to see how far corrosion has proceeded. Such methods are relevant especially to professional applications of the invention.

BRIEF DESCRIPTION OF THE DRAWING

The invention is explained in further detail, by way of example and with reference to the accompanying drawing, wherein.

Throughout the Figures, similar or corresponding features are indicated by same reference numerals.

DETAILED EMBODIMENTS

Figure 1:
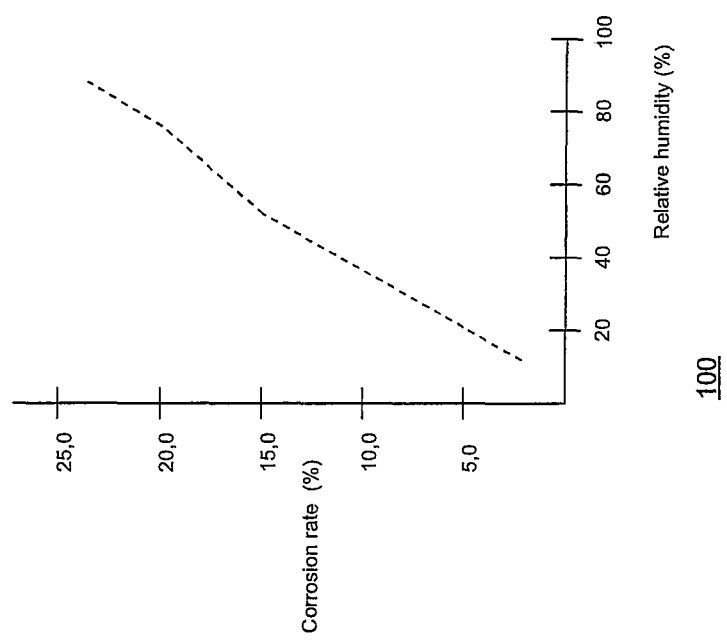
FIG. 1 is a diagram illustrating a roughly linear dependence of the corrosion rate on relative humidity.

FIG. 1 is a diagram 100 showing the relationship between corrosion rate (in percentages) and relative humidity (in percentages), measured for a temperature between, say, 20°-30° C. The diagram is based on the publication of Lin and Zhang mentioned above. The dependence is roughly linear over the range of relative humidity.

Figure 2:
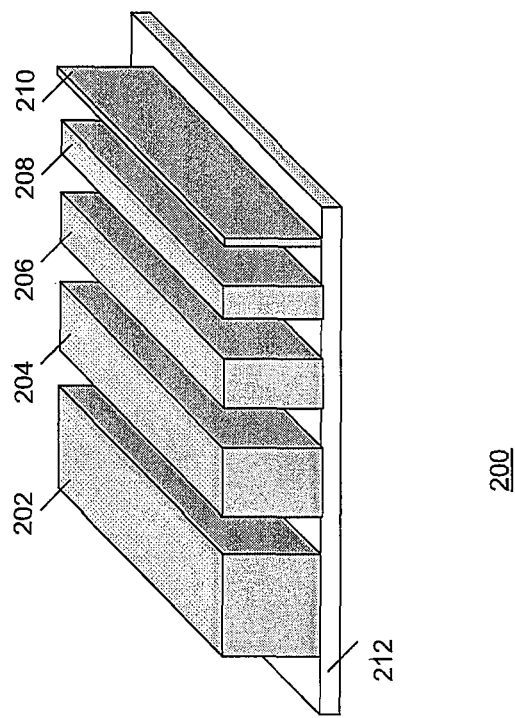
FIGS. 2-10 are diagrams of examples of sensor configurations in the invention.

FIG. 2 is a diagram of an array 200 of differently sized strips 202, 204, 206, 208 and 210 of a material sensitive to corrosion for use in a humidity sensor according to the invention. Strips 202-210 are formed on a substrate 212. Typically, array 200 is manufactured in a semiconductor process, e.g., CMOS, using lithographic exposure and dry-etching, on substrate of a semiconductor material, e.g., silicon. The material that forms strips 202-210 comprises, e.g., a metal that is conventionally deposited in such a process to form interconnects. Preferably, the spaces between strips 202-210 are filled with another material (not shown) that is much less sensitive to corrosion than the material forming strips 202-210. This leaves the upper surfaces of strips 202-210 exposed to corrosion, until the material has corroded all the way down to substrate 212, e.g., all the way down or laterally (from left to right and from right to left in the drawing from the strip's edges).

Figure 3:
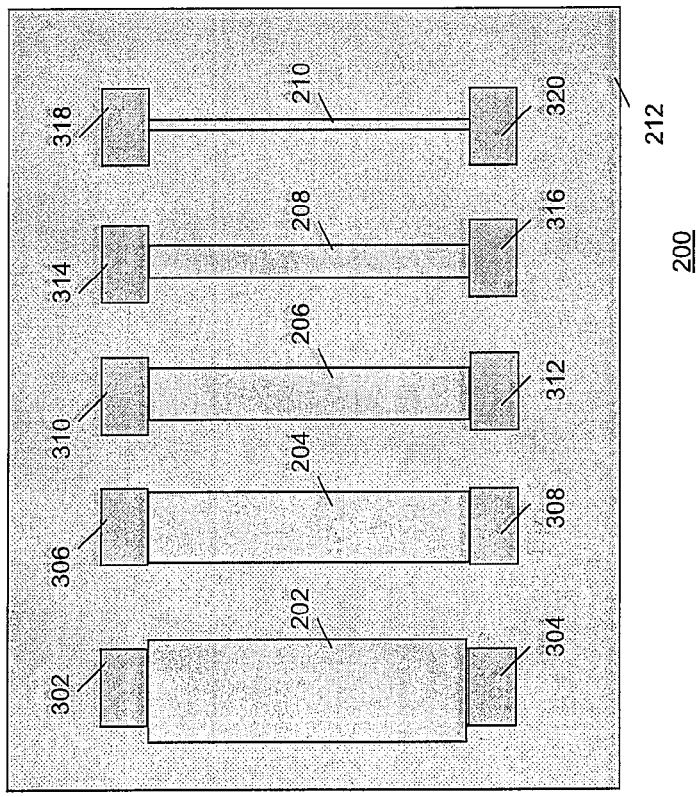

FIG. 3 shows array 200 wherein strips 202-210 are connected to respective pairs of bonding pads 302, 304, 306, 308, 310, 312, 314, 316, 318 and 320. Corrosion affects the resistance of any of strips 202-210. The strip's upper surface collects moisture that together with certain airborne chemicals (e.g., in dust collected on the upper surface) causes the upper surface to deteriorate until the corrosion has eaten away the strip's material. When exposed to dust and moisture, the strip's resistance changes over time. Now, by giving strips 202-210 different areas at their upper surface as shown in the drawing, and/or different thicknesses as measured from substrate 212 upwards, the order wherein strips 202-210 fail to electrically conduct properly can be pre-set, assuming that the combined upper surface of strips 202-210 is exposed uniformly to corrosion. Accordingly, strips 202-210 fail one after the other starting with the one that is the more sensitive, in this case strip 210 being the narrower one of strips 202-210. This is shown in FIG. 4 wherein the material of strip 210 has vanished at locations 402 and 404, so that a current between pads 318 and 320 is interrupted.

If pads 302-320 are connected to a circuit (not shown) that in effect measures the resistance per strip, either continuously or repeatedly, the accumulated resistance measurements represent the history of exposure to humidity. The circuit may be part of the sensor accommodating array 200 or, alternatively, may be a device external to the sensor, the sensor then providing a suitable interface to connect with the circuit.

Figure 4:
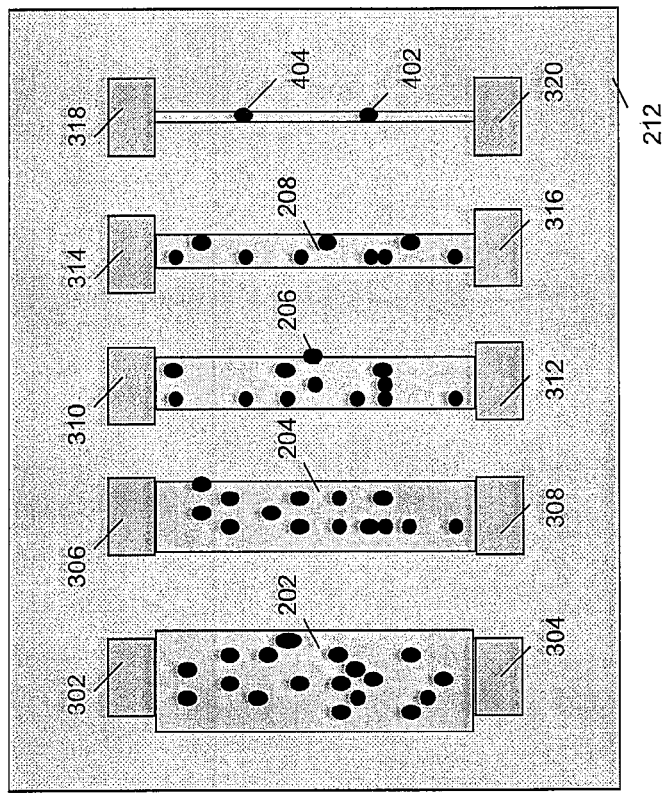
Figure 6:
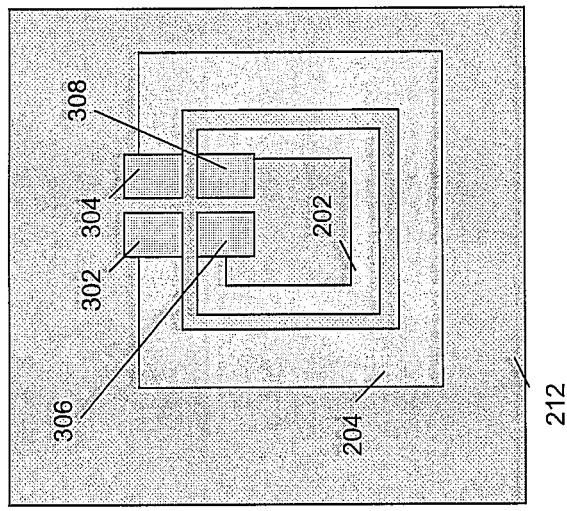
Figure 5:
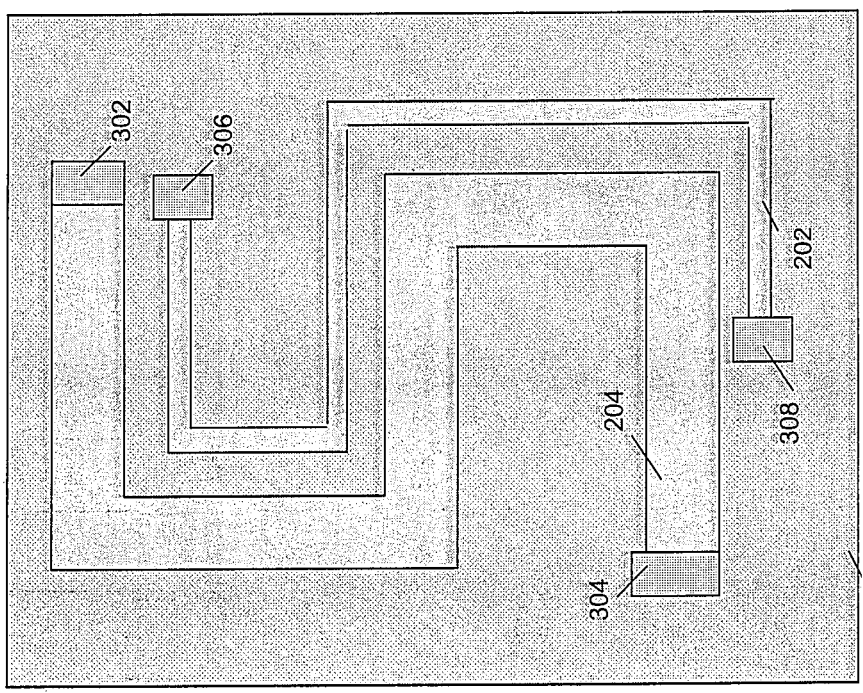
Figure 7:
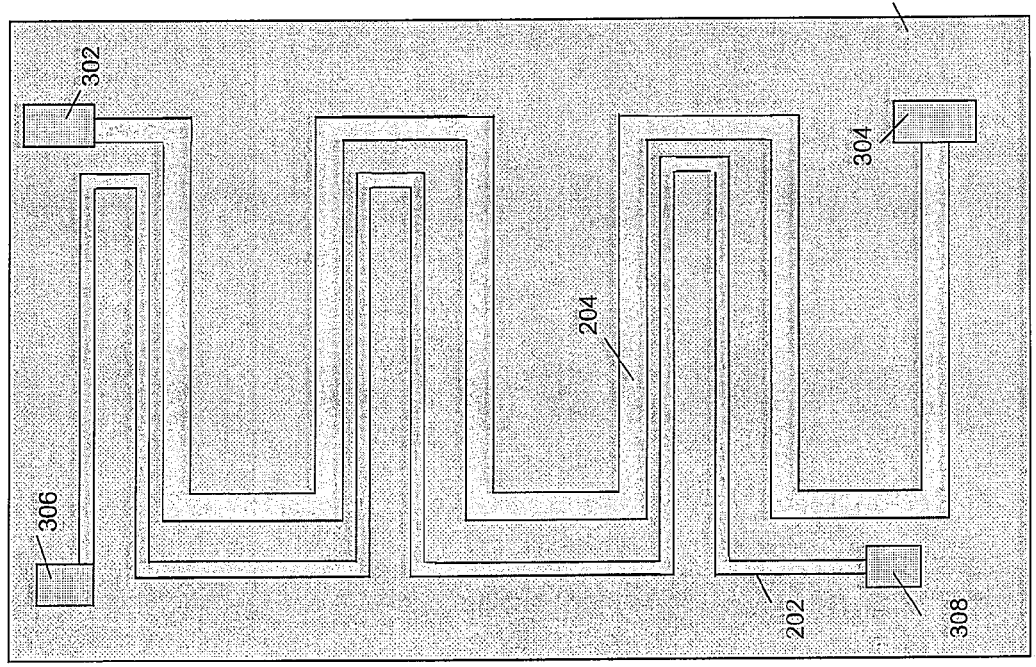

FIGS. 2-4 show an embodiment with rectangular strips 202-210 arranged in parallel. Other spatial configurations can be used instead, e.g., so as to at least partly cancel out a possible dependence of the exposure to corrosion on the strip's location at substrate 212. FIGS. 5, 6 and 7 show examples of such configurations 500, 600 and 700, respectively, each being shown with only two strips 202 and 204 so as not to obscure the drawing. Configuration 500 illustrates strips 202 and 204 meandering across substrate 212. Configuration 600 shows strips 202 and 204 arranged in a concentric fashion. In configuration 500, strips 202 and 204 have the same path length between their respective contacts. In configuration 600, strips 202 and 204 have different path lengths. Their surface areas exposed to corrosion can be made different by, e.g., keeping the same width or even having the longer one of the strips have a wider path. Alternatively, their exposed surfaces can be made the same by giving the longer strip a proportionally narrower width. Configuration 700 uses an interleaved, or interdigitized, layout, wherein each of electrodes 202 and 204 forms a comb-shaped structure that meshes with the comb-shaped structure of the other. Configuration 700 can be used when relatively long strips are required or when each strip should cover a relatively large surface area of die 212.

Figure 8:
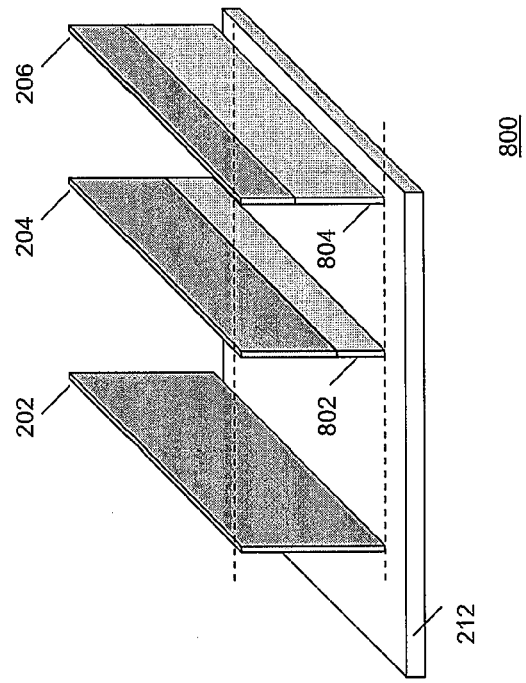

FIG. 8 illustrates a configuration of strips 202-206 arranged in parallel, being of uniform length and width, but having different thicknesses (measured in the direction perpendicular to substrate 212). Strip 202 rests on substrate 212, whereas a lower basis 802 is set between substrate 212 and strip 204, and a higher basis 804 is set between strip 206 and substrate 212. The spaces between strips 202-206 are shown here as void, but comprise material that is less sensitive to corrosion than the material of strips 202-206 in operational use of the sensor. Such a configuration can be implemented in, e.g., a semiconductors manufacturing technology.

In the previous FIGS. 2-8, substrate 212 has been shown as relatively small with respect to strips 202-210 for convenience only. Substrate 212 may be larger to accommodate additional electrical or electronic circuitry.

Figure 9:
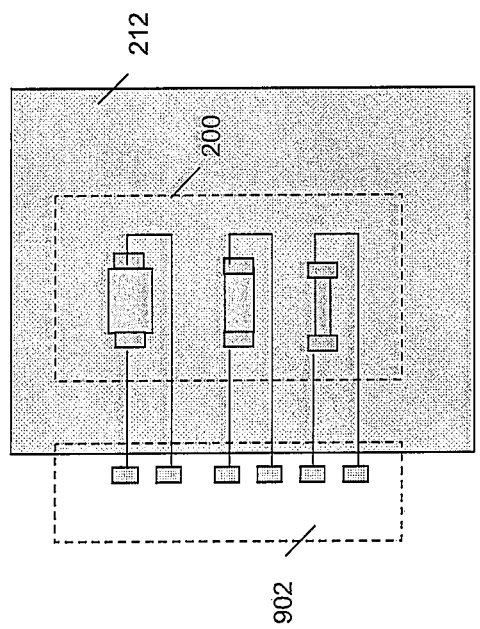

In FIG. 9, a device 900 is shown for a sensor of the invention. Device 900 comprises configuration 200, discussed above. The strips in configuration 200 are not individually indicated here, in order to not obscure the drawing. Device 900 is provided with an interface 902, e.g., a galvanic interface, for connecting an external measuring apparatus (not shown), e.g., a multimeter, to each of the strips in configuration 900. Repeated measuring of the resistance of each individual strip between suitably long time intervals gives insight in the progressive corrosion of the strips' material, and hence in the accumulated exposure to the corrosive influences of the sensor's environment. The measuring can include manually connecting a connector of a measuring apparatus to interface 902 each time a measurement is taken. Alternatively, a measuring apparatus (not shown) remains connected to interface 902 for the duration of operational use of device 900 as sensor. The measuring apparatus automatically and repeatedly measures the resistances of the strips between different time intervals, and possibly stores the measurement results in a memory (not shown). Alternatively, or in addition, the measuring apparatus generates a signal when the most recent measurement matches a pre-set condition. The signal then is an indication for a human operator or for automated equipment to take action with respect to a product for which this particular device monitors the environment. For example, the product is to be removed from an inventory of similar products once the accumulated exposure to the environment has reached a predetermined level, represented by the most recent resistance measurement.

Figure 10:
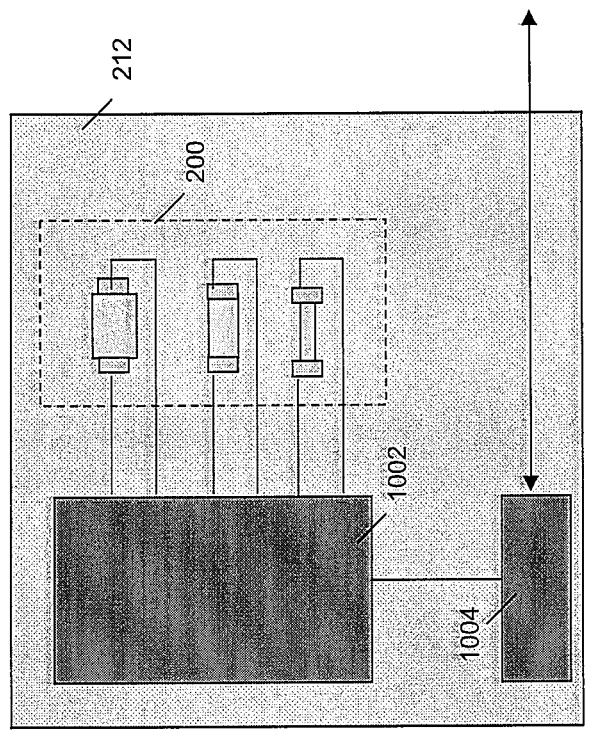

FIG. 10 shows a configuration 1000 with a more integrated approach. Now, additional circuitry 1002 has been accommodated on substrate 212 for measuring continuously or repeatedly the Ohmic resistances of the strips in configuration 200. Circuitry 1002 processes these measurements so as to generate data or a signal representative of the measurements. In an embodiment, this data or this signal is generated conditionally, e.g., if circuitry 1002 decides that the most recent measurement is indicative of the accumulated exposure to the environment has reached a certain level. The data or signal generated by circuitry 1002 is supplied to an agent external to configuration 1000 via a suitable interface 1004, e.g., via an RF interface. Preferably, this data or signal also carries an identification of configuration 1000, e.g., in case multiple of such configurations 900 are being used to track exposure of multiple products or to track exposure at multiple locations within a certain room or space. Configuration 1000 thus operates autonomously and requires a power supply. This power supply is built-in or, alternatively, power is generated locally at configuration 1000 using, e.g., incident electromagnetic radiation as a power source.

In summary, a sensor of the invention senses a characteristic of an environment, e.g., humidity. The sensor has a substrate with strips of material that is sensitive to corrosion as a result of the characteristic. The strips are configured to respond differently to the characteristic. By means of repeatedly measuring the resistances of the strips, the environment can be monitored in terms of accumulated exposure to the characteristic. The strips are manufactured in a semiconductor technology so as to generate accurate sensors that behave predictably.

The invention claimed is:

1. A device including a sensor for sensing a characteristic of an environment of the sensor, comprising:
   a substrate;
   at least two corrosive-sensitive strips disposed on the substrate, the corrosive-sensitive strips differing in metal-based material type and being sensitive to corrosion as a result of the characteristic, each of the at least two corrosive-sensitive strips being configured and arranged to corrode at different non-zero rates; and
   at least two pairs of two contacts arranged between each of the at least two corrosive-sensitive strips and configured and arranged to measure an impedance of each strip, the impedance being indicative of the respective rates at which the strips corrode and thereby indicating the characteristic of the environment.

2. The device of claim 1, further including:
   at least one additional corrosive-sensitive strip arranged between two further contacts for measuring the impedance of the additional strip; and
   wherein the at least one additional corrosive-sensitive strip is configured to have impedances that respond differently to the characteristic and is different in terms of thickness or material type.

3. The device of claim 2, wherein:
   a path length between the contacts of the corrosive-sensitive strip and a further path length between the further contacts of the additional corrosive-sensitive strip are substantially the same; and
   the corrosive-sensitive strip and the additional corrosive-sensitive strip have different sizes of area exposed to the environment.

4. The device of claim 2, wherein the material of the corrosive-sensitive strip and the material of the additional corrosive-sensitive strip are chemically the same.

5. The device of claim 2, wherein the material of the corrosive-sensitive strip and the material of the additional corrosive-sensitive strip are chemically different.

6. The device of claim 2, wherein the corrosive-sensitive strip and the additional corrosive-sensitive strip have different thicknesses as measured from the substrate to respective surfaces of the strip and of the additional strip exposed to the characteristic.

7. The device of claim 1, wherein the characteristic includes humidity.

8. The device of claim 1, wherein the corrosive-sensitive strip is configured so as to form a path between the two contacts that is longer than the shortest path between the contacts.

9. The device of claim 1, wherein the corrosive-sensitive strip is configured so as to form a path between the two contacts that is the shortest path between the contacts.

10. The device of claim 1, wherein the corrosive-sensitive strip is manufactured in a semiconductors technology process, wherein the at least two corrosive-sensitive strips are different in terms of thickness and material type.

11. The device of claim 1, wherein the at least two corrosive-sensitive strips are interdigitized to form a comb-shaped structure.

12. The device of claim 1, wherein the at least two corrosive-sensitive strips are arranged in meandering paths across the substrate.

13. The device of claim 1, wherein the at least two corrosive-sensitive strips are arranged in a concentric pattern on the substrate.

14. A method of sensing a characteristic of an environment, the method comprising:
   providing at least two corrosive-sensitive strips of material that differ in metal-based material type and are sensitive to corrosion at different non-zero rates as a result of the characteristic, wherein the strip is arranged between at least one pair of two contacts;
   measuring an impedance of the least two corrosive-sensitive to indicate degradation due to corrosion; and
   using the respective rates of corrosion to indicate the characteristic of the environment.

15. The method of claim 14, comprising:
   using an additional corrosive-sensitive strip sensitive to corrosion;
   the at least two corrosive-sensitive strips and the additional corrosive-sensitive strip configured to have impedances that respond differently to the characteristic;

measuring the impedances of the corrosive-sensitive strip and the additional corrosive-sensitive strip on at least two different moments; and comparing the respective impedance measurements with calibration or reference information, prepared in advance, to determine progress of corrosion.

16. The method of claim 14, wherein the at least two corrosive-sensitive strips are different in terms of thickness and material type.

17. The method of claim 14, wherein the at least two corrosive-sensitive strips are different in terms of thickness and material type.

* * * * *